US012603470B2

(12) United States Patent
Kim et al.

(10) Patent No.: US 12,603,470 B2
(45) Date of Patent: Apr. 14, 2026

(54) APPARATUS AND METHOD FOR EMITTING MULTI-WAVELENGTH LASER

(71) Applicant: WONTECH Co., Ltd., Daejeon (KR)

(72) Inventors: Jong Won Kim, Seongnam-si (KR); Jung Hyun Kim, Seongnam-si (KR); Young Seok Seo, Sejong-si (KR); Dong Hyun Lee, Daejeon (KR)

(73) Assignee: WONTECH Co., Ltd., Daejeon (KR)

( * ) Notice: Subject to any disclaimer, the term of this patent is extended or adjusted under 35 U.S.C. 154(b) by 286 days.

(21) Appl. No.: 18/472,117

(22) Filed: Sep. 21, 2023

(65) Prior Publication Data

US 2025/0007230 A1     Jan. 2, 2025

(30) Foreign Application Priority Data

Jun. 29, 2023     (KR) ........................ 10-2023-0084468

(51) Int. Cl.
*A61N 5/067*          (2006.01)
*A61N 5/06*           (2006.01)
(Continued)

(52) U.S. Cl.
CPC .......... *H01S 3/0407* (2013.01); *A61N 5/0616* (2013.01); *A61N 5/067* (2021.08);
(Continued)

(58) Field of Classification Search
CPC .................. A61N 5/0616; A61N 5/067; A61N 2005/0626; A61N 2005/0659; H01S 3/2391
(Continued)

(56) References Cited

U.S. PATENT DOCUMENTS

2004/0202211 A1*   10/2004   Paetzel ................... H01S 3/041
                                                              372/55
2013/0268031 A1*   10/2013   Ko ....................... A61N 5/0616
                                                              607/80
(Continued)

FOREIGN PATENT DOCUMENTS

JP          2022-536456 A      8/2022
KR      10-2012-0052446 A      5/2012
(Continued)

OTHER PUBLICATIONS

KR Office Action.
International Search Report.
JP Office Action dated Apr. 28, 2025.

*Primary Examiner* — Nathan J Jenness
(74) *Attorney, Agent, or Firm* — Harvest IP Law, LLP

(57)          ABSTRACT
Proposed are an apparatus and a method for emitting multi-wavelength lasers. The apparatus for emitting multi-wavelength lasers includes a main body configured to perform overall control and operation, a handpiece which is operated by the control of the main body and is connected to the main body by wire, and a tip capable of being coupled to one side of the handpiece, wherein the main body includes a first power supply part, a display part, a control part, a laser generation part, a temperature control part, and a cooling part, wherein the laser generation part includes a first laser generator and a second laser generator which output lasers of different wavelengths, respectively, and the temperature control part includes a first temperature control part which controls a temperature of the first laser generator, and a second temperature control part which controls a temperature of the second laser generator.

17 Claims, 7 Drawing Sheets

(51) Int. Cl.

| | |
|---|---|
| *H01S 3/04* | (2006.01) |
| *H01S 3/042* | (2006.01) |
| *H01S 3/16* | (2006.01) |
| *H01S 3/23* | (2006.01) |

(52) U.S. Cl.
CPC ............ *H01S 3/0404* (2013.01); *H01S 3/042* (2013.01); *H01S 3/1611* (2013.01); *H01S 3/1633* (2013.01); *H01S 3/1643* (2013.01); *H01S 3/2391* (2013.01); *A61N 2005/0626* (2013.01); *A61N 2005/0659* (2013.01); *H01S 2302/00* (2013.01)

(58) Field of Classification Search
USPC ...................................................... 607/88–95
See application file for complete search history.

(56) References Cited

U.S. PATENT DOCUMENTS

| | | | | |
|---|---|---|---|---|
| 2020/0112137 A1 * | 4/2020 | Arakawa | ............ | G02B 27/0927 |
| 2020/0391051 A1 * | 12/2020 | Daly | .................... | A61N 5/0625 |
| 2021/0059753 A1 * | 3/2021 | Tankovich | ............. | A61N 5/067 |
| 2021/0260401 A1 * | 8/2021 | Thorhauge | ........... | G02F 1/3534 |
| 2021/0376553 A1 * | 12/2021 | Shang | ................. | H01S 3/09415 |

FOREIGN PATENT DOCUMENTS

| | | | | |
|---|---|---|---|---|
| KR | 10-2016-0146337 A | 12/2016 | | |
| KR | 10-1728770 B1 * | 4/2017 | ............. | A61B 18/00 |
| KR | 10-2019-0044221 A | 4/2019 | | |
| KR | 10-2020-0057388 A | 5/2020 | | |

\* cited by examiner

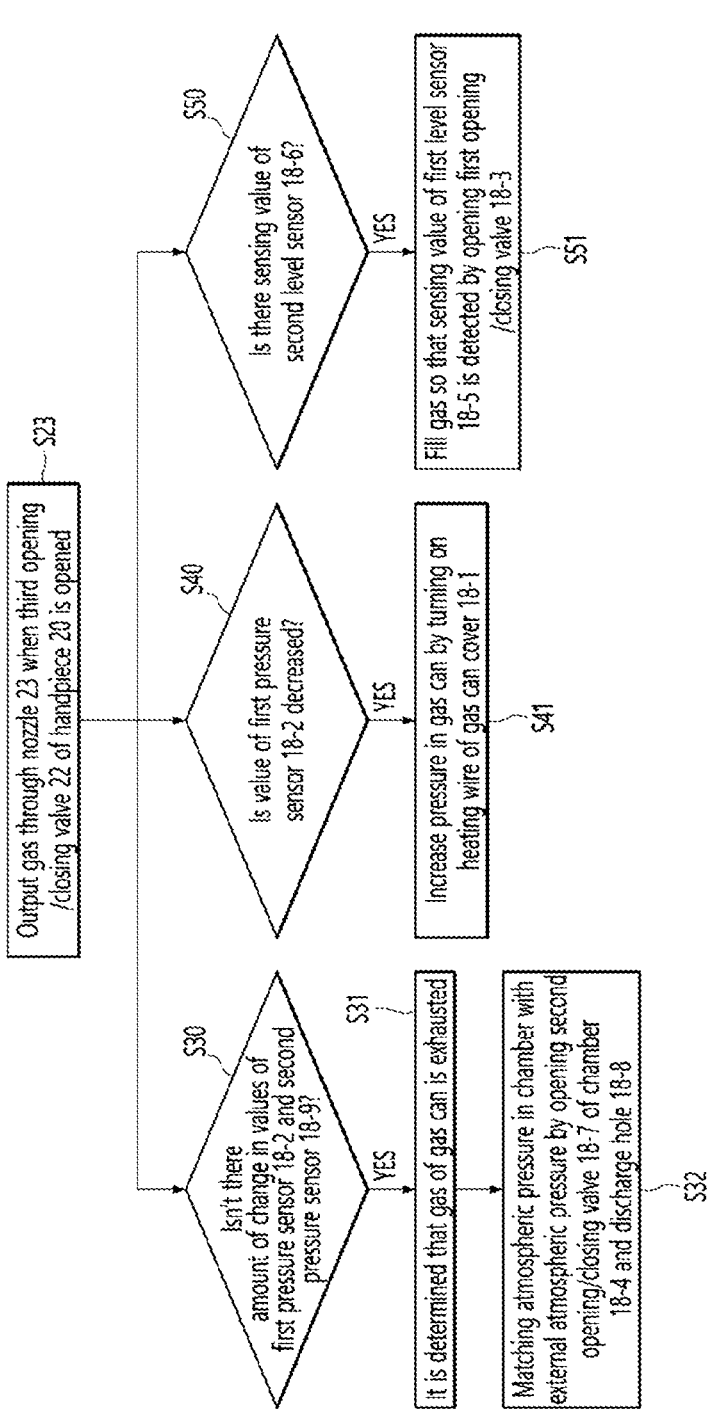

Output gas through nozzle 23 when third opening /closing valve 22 of handpiece 20 is opened — S23

Isn't there amount of change in values of first pressure sensor 18-2 and second pressure sensor 18-9? — S30

Is value of first pressure sensor 18-2 decreased? — S40

Is there sensing value of second level sensor 18-6? — S50

It is determined that gas of gas can is exhausted — S31

Increase pressure in gas can by turning on heating wire of gas can cover 18-1 — S41

Fill gas so that sensing value of first level sensor 18-5 is detected by opening first opening /closing valve 18-3 — S51

Matching atmospheric pressure in chamber with external atmospheric pressure by opening second opening/closing valve 18-7 of chamber 18-4 and discharge hole 18-8 — S32

APPARATUS AND METHOD FOR EMITTING MULTI-WAVELENGTH LASER

CROSS REFERENCE TO RELATED APPLICATION

The present application claims priority to Korean Patent Application No. 10-2023-0084468, filed Jun. 29, 2023, the entire contents of which are incorporated herein for all purposes by this reference.

BACKGROUND OF THE INVENTION

Field of the Invention

The present disclosure relates generally to an apparatus for emitting a laser. More particularly, the present disclosure relates to an apparatus and a method for emitting multi-wavelength lasers, in which multi-wavelength lasers are simultaneously emitted.

Description of the Related Art

The use of electromagnetic radiation in the visible and infrared spectral regions has become a common technique in many fields of industry, medicine, and research. For example, such radiation is becoming increasingly important in the field of dermatology. In many cases, a laser source is used to generate a desired radiation level at a required wavelength.

There are many lasers commonly used for dermatological applications such as treatment of vascular or pigmented lesions, hair removal, and skin peeling. The principle of selective photothermal dissolution underlies many laser treatments and is used to treat several conditions such as varicose veins, flaming nevus, other opacifying vascular lesions and pigmented lesions, including tattoos. Dermal and epidermal layers containing a target structure are usually irradiated with light from a laser or flash lamp. The wavelength of this light is selected such that its energy is preferentially or selectively absorbed within the structure. This creates local heating with the intention of raising a temperature to a point at which constituent proteins are denatured or pigment particles diffuse.

A skin treatment device for improving skin conditions by irradiating the skin of a subject with lasers of various wavelengths is known.

Examples of lasers used in such a skin treatment device include lasers with wavelengths of 1064 nm and 755 nm. The 1064 nm wavelength laser acts on blood vessels in the dermis, and can achieve hair removal and skin regeneration effects regardless of skin color. That is, such a 1064 nm wavelength laser is useful for dermal blood vessel treatment because the laser has a deep skin penetration depth and high oxyhemoglobin absorption. In addition, since the 1064 nm wavelength laser does not have high melanin absorption, an excellent hair removal effect can be obtained even for dark-skinned subjects. In addition, the 1064 nm wavelength laser not only has a deep penetration depth but also has a high absorption rate, and thus stimulates collagen in the dermal layer. As a result, the 1064 nm wavelength laser has a high effect of improving fine wrinkles and regenerating the skin.

A laser with a wavelength of 755 nm has a whitening effect on the epidermis and shows a high hair removal effect in subjects with light skin color. That is, the 755 nm wavelength laser has a slightly shallower penetration depth than the 1064 nm wavelength laser, but has higher melanin absorption, so the hair removal effect thereof is superior to that of the 1064 nm wavelength laser. However, due to the high melanin absorption, the 755 nm wavelength laser is limited to a skin color type. The 755 nm wavelength laser cannot be used on dark-skinned subjects because the skin absorbs energy first, which damages the skin. On the other hand, the 755 nm wavelength laser has high melanin absorption and thus has the whitening effect of brightening the skin.

When the above 1064 nm and 755 nm wavelength lasers are combined and emitted to a subject, blood vessel treatment, hair removal, and whitening effects can be improved in response to skin penetration depth and skin color. For this reason, recent skin treatment devices using lasers are implemented to simultaneously or alternately emit lasers of at least two wavelengths.

In this case, in order to increase the output efficiency of lasers of different wavelengths, it is necessary to delicately control the temperature of a laser generating device, and in order to relieve pain after a laser is emitted, cooling gas output. In this case, in order to normally output the cooling gas, it is necessary to control the internal pressure of an internal cooling gas output structure.

SUMMARY OF THE INVENTION

Accordingly, the present disclosure has been made keeping in mind the above problems occurring in the related art, and the present disclosure is intended to propose an apparatus and a method for emitting multi-wavelength lasers, in which a 1064 nm wavelength laser and a 755 nm wavelength laser are emitted simultaneously or alternately, a temperature inside a laser resonator is controlled by using cold/hot water for maximum efficiency of laser output, and cooling gas is output to relieve pain after the laser output, when pressure in a gas flow path inside the product is controlled for the output of the cooling gas.

In order to achieve the above objectives, according to one aspect of the present disclosure, there is provided an apparatus for emitting multi-wavelength lasers, the apparatus including: a main body configured to perform overall control and operation; a handpiece which is operated by the control of the main body and is connected to the main body by wire; and a tip capable of being coupled to one side of the handpiece, wherein the main body includes: a first power supply part configured to enable the overall operation; a display part which operates by receiving power from the first power supply part and provides a detailed procedure screen and a detailed procedure setting control screen to a patient and an operator; a control part which operates by receiving power from the first power supply part and controls the overall operation according to a detailed procedure setting value of the display part; a laser generation part which receives power from the first power supply part, operates according to the control of the control part, and generates a laser; a temperature control part which operates by receiving power from the first power supply part and maintains an appropriate temperature to increase laser output efficiency when generating a laser in the laser generation part; and a cooling part which operates by receiving power from the first power supply part and outputs cooling gas to a patient's skin, wherein the laser generation part includes a first laser generator and a second laser generator which output lasers of different wavelengths, respectively, and the temperature control part includes a first temperature control part which controls a temperature of the first laser generator, and a second temperature control part which controls a temperature of the second laser generator.

The first laser generator may generate a laser with a wavelength of 720 nm to 780 nm, and the second laser generator may generate a laser with a wavelength of 955 nm to 1100 nm.

Each of the first laser generator and the second laser generator may include: multiple lamps; a gain medium configured to absorb light generated from the lamps; and a reflection part having one pair of mirrors facing each other at horizontally opposite ends of the gain medium to resonate light on the gain medium.

One mirror of the first laser generator may have a reflectance of at least 97%, and one remaining mirror thereof may have a reflectance of 78% to 83%.

One mirror of the second laser generator may have a reflectance of at least 97%, and one remaining mirror thereof may have a reflectance of 38% to 43%.

Instead of the reflection part, the opposite ends of the gain medium may be used by being coated by applying the same reflectances as described above.

The first temperature control part may include: a first cooling water chamber which provides or accommodates cooling water circulating through a pipe inside the first laser generator to maintain temperatures of a lamp of the first laser generator and a gain medium at appropriate temperatures; a first heating part which increases a temperature of the first cooling water chamber, and a first cooling fan which decreases the temperature of the first cooling water chamber, and the second temperature control part may include: a second cooling water chamber which provides or accommodates cooling water circulating through a pipe inside the second laser generator to maintain temperatures of a lamp of the second laser generator and the gain medium at appropriate temperatures; a second heating part which increases a temperature of the second cooling water chamber; and a second cooling fan which decreases the temperature of the second cooling water chamber.

The cooling part may include: a gas can cover which is attached inside the main body and into which a gas can is inserted; a first hose which is coupled to a lower end of the gas can cover and is used as a flow path through which gas of the gas can flows; a first pressure sensor which is coupled to a lower part of the gas can cover, operates with power from the first power supply part, and checks whether the gas can is inserted into the gas can cover, a chamber which is coupled to one side of the first hose and stores cooling gas; a first opening/closing valve which controls gas output in a center portion of the first hose except for opposite ends of the first hose located between the gas can cover and the chamber and operates with the power of the first power supply part and the control of the control part; a first level sensor which is coupled to one side of an upper end of the chamber, detects whether there is gas therein, and operates with the power of the first power supply part and the control of the control part; a second level sensor which is coupled to one side of a lower end of the chamber, detects whether there is gas therein, and operates with the power of the first power supply part and the control of the control part; a discharge hole which is coupled to one side surface of the chamber and is configured to discharge gas in the chamber to the outside; a second opening/closing valve which opens the discharge hole to discharge gas in the chamber to the outside and operates with the power of the first power supply part and the control of the control part; a second pressure sensor which is coupled to a lower end of an inner center of the chamber and checks whether there is gas in the chamber;

and a second hose which connects the chamber with the handpiece and is used as a flow path of cooling gas.

The handpiece may include a corrective lens which is provided on one end of the handpiece and corrects a dispersed laser beam to be parallel.

The tip may include a lens part for outputting a laser generated in the main body, with the laser having a preset laser output spot size.

The lens part of the tip may include one or more and less than five lenses therein, wherein each of the lenses may be formed to be concave on one surface thereof and convex on a remaining surface thereof, to be concave on the opposite surfaces thereof, or to be convex on the opposite surfaces, and the lenses may be combined according to a size of a laser irradiation beam.

According to another aspect of the present disclosure, there is provided a method for emitting multi-wavelength lasers, the method including: transmitting power to a second power supply part of the handpiece after the first power supply part of the main body is turned on; determining whether a laser output signal is input in a controller of the handpiece; generating a laser by operating the laser generation part according to controls of the display part and the control part when it is determined that a laser output signal is input in the determining of whether a laser output signal is input in the controller of the handpiece; generating a laser with a wavelength of 720 nm to 780 nm in the first laser generator and generating a laser with a wavelength of 955 nm to 1100 nm in the second laser generator, with the laser generation part operating according to the controls of the display part and the control part; performing an operation for maintaining a temperature in the temperature control part to maintain appropriate temperatures of the first and second laser generators when the first laser generator and the second laser generator generate the lasers; irradiating a patient with a laser generated in the laser generation part through the tip after the laser is transmitted through an optical fiber to the handpiece; outputting cooling gas to a nozzle of the handpiece from the cooling part of the main body; determining whether a laser output signal is input in the controller of the handpiece; and returning to the generating of a laser by operating the laser generation part according to the controls of the display part and the control part when it is determined that a laser output signal is input in the determining of whether a laser output signal is input in the controller of the handpiece.

In the performing of the operation for maintaining a temperature in the temperature control part to maintain the appropriate temperatures of the laser generators, the temperature control part may include the first temperature control part which controls the temperature of the first laser generator, and the second temperature control part which controls the temperature of the second laser generator.

The first temperature control part may maintain the temperature of the first laser generator at 50° C. to 65° C., and the second temperature control part may maintain the temperature of the second laser generator at 20° C. to 35° C.

The method may further include: collimating a dispersed laser beam by using a corrective lens before the handpiece transmits a laser to the tip in the irradiating of a patient with a laser generated in the laser generation part through the tip after the laser is transmitted through the optical fiber to the handpiece.

The method may further include: coupling the gas can to the gas can cover of the cooling part of the main body; closing the first opening/closing valve when a sensing value of the first level sensor is detected after the first opening/ closing valve is opened and gas is filled up to the first level sensor of the chamber when the gas can is coupled to the gas can cover and the coupling of the gas can is sensed by the first pressure sensor; determining whether a patient is irradiated with a laser in the control part of the main body; and outputting gas to a patient through the nozzle by opening a third opening/closing valve of the handpiece when it is determined that the patient is irradiated with the laser in the determining of whether the patient is irradiated with the laser in the outputting of cooling gas to the nozzle of the handpiece from the cooling part of the main body.

The method may further include: determining whether there is an amount of change in values of the first pressure sensor and the second pressure sensor; determining that gas inside the gas can is exhausted when it is determined that there is no amount of change in the values of the first pressure sensor and the second pressure sensor in the determining of whether there is the amount of change in the values of the first pressure sensor and the second pressure sensor; and matching atmospheric pressure inside the chamber with external atmospheric pressure by opening the second opening/closing valve of the chamber and the discharge hole in the outputting of gas to a patient through the nozzle by opening the third opening/closing valve of the handpiece.

In the irradiating of a patient with a laser generated in the laser generation part through the tip after the laser is transmitted through the optical fiber to the handpiece, as the laser with which the patient is irradiated, the laser with a wavelength of 720 nm to 780 nm generated in the first laser generator and the laser with a wavelength of 955 nm to 1100 nm generated in the second laser generator may be emitted simultaneously.

As the laser with which the patient is irradiated, the laser with a wavelength of 720 nm to 780 nm generated in the first laser generator and the laser with a wavelength of 955 nm to 1100 nm generated in the second laser generator may be emitted simultaneously or with a time difference of 200 ms therebetween.

According to these features, the laser irradiation apparatus of the present disclosure can output a laser with maximum efficiency by maintaining an appropriate internal temperature of each of the laser generators.

In addition, pain can be reduced by outputting cooling gas after emitting a laser. In this case, to output the cooling gas, the pressure of a gas flow path inside the main body is controlled, thereby facilitating the output of the cooling gas and lowering the risk of explosion of the gas can due to the control of the pressure of the internal gas flow path.

In addition, a 755 nm wavelength laser and a 1064 nm wavelength laser can be simultaneously emitted or an irradiation time difference therebetween can be varied up to 200 ms, thereby enabling detailed control according to skin characteristics and skin color.

BRIEF DESCRIPTION OF THE DRAWINGS

The above and other objectives, features, and other advantages of the present disclosure will be more clearly understood from the following detailed description when taken in conjunction with the accompanying drawings, in which:

Figure 4:
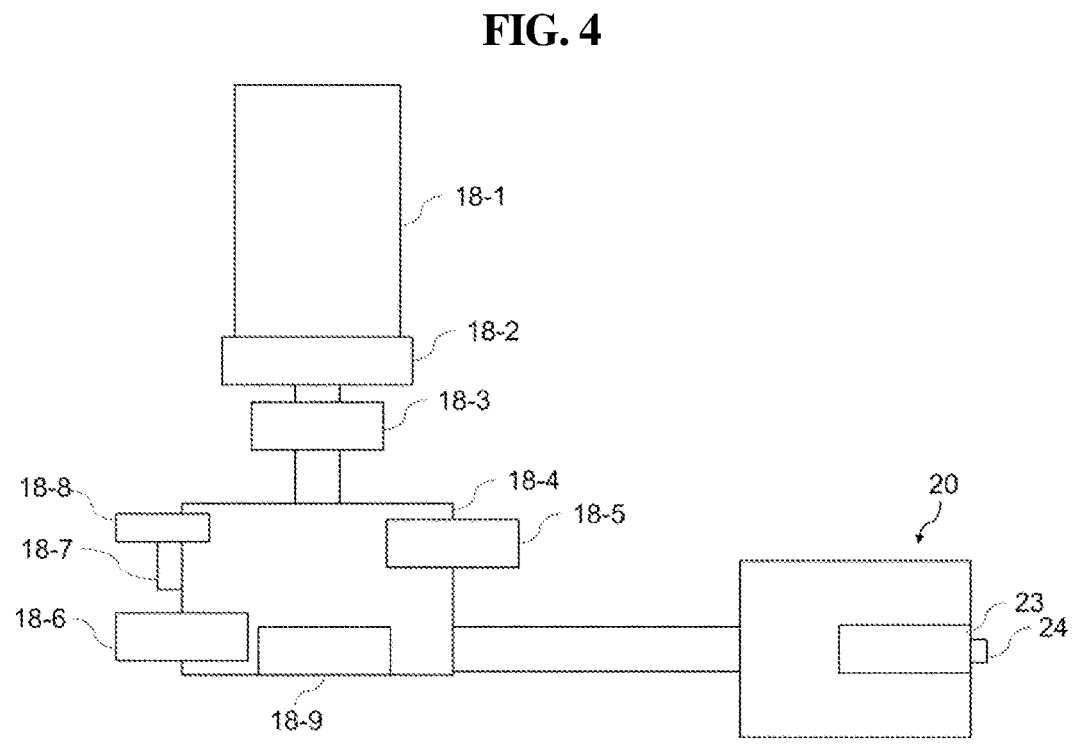

FIG. 4 is a schematic diagram illustrating the cooling part and a cooling flow path in the apparatus for emitting multi-wavelength lasers according to the embodiment of the present disclosure;

FIG. 7 is a flowchart of a method for controlling pressure in a main body in the method for emitting multi-wavelength lasers according to the embodiment of the present disclosure.

DETAILED DESCRIPTION OF THE INVENTION

Figure 1:
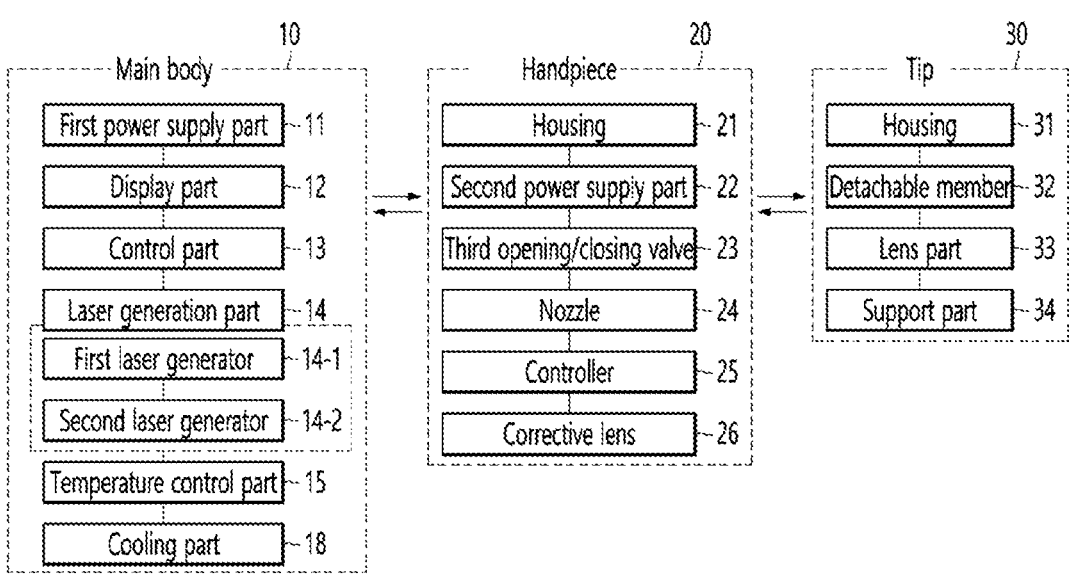
FIG. 1 is a configuration diagram of an apparatus for emitting multi-wavelength lasers according to an embodiment of the present disclosure.

Hereinafter, with reference to the accompanying drawings, an embodiment of the present disclosure will be described in detail so that a person having ordinary knowledge in the technical field to which the present disclosure belongs can easily practice the embodiment. However, the present disclosure may be implemented in many different forms and is not limited to the embodiment described herein. In addition, in order to clearly describe the present disclosure, parts irrelevant to the description are omitted in the drawings, and similar reference numerals are given to similar parts throughout the specification.

Throughout the specification, when a part is said to be "connected (coupled, contacted, or combined)" with another part, this includes cases in which a part is not only "directly connected", but also "indirectly connected" with another member therebetween. In addition, when a component is said to "include" another component, this means that it may further include other components without excluding the other components unless otherwise stated.

Terms used in this specification are only used to describe specific embodiment, and are not intended to limit the present disclosure. Singular expressions include plural expressions unless the context clearly indicates otherwise. In this specification, terms such as "include" or "have" are intended to indicate that there is feature, number, step, operation, component, part, or combination thereof described in the specification, but it should be understood that the terms do not preclude the possibility of the presence or addition of one or more other features, numbers, steps, operations, components, parts, or combinations thereof.

Hereinafter, an apparatus and a method for emitting multi-wavelength lasers according to an embodiment of the present disclosure will be described with reference to the accompanying drawings.

Figure 2:
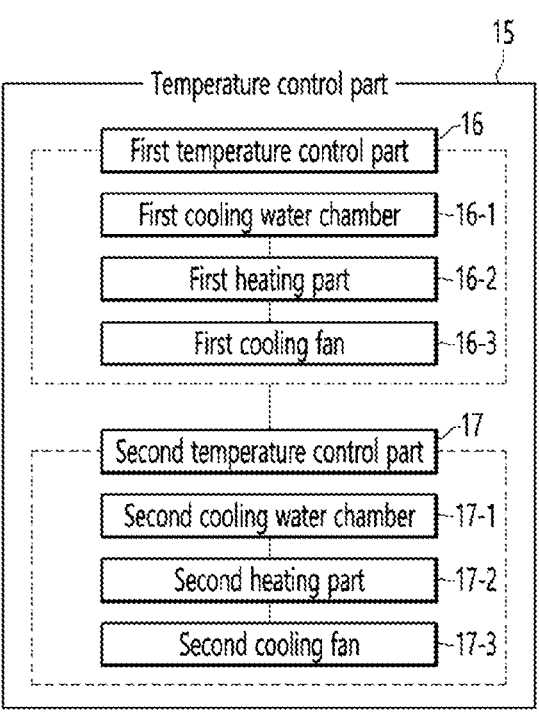
FIG. 2 is a configuration diagram of a temperature control part in the apparatus for emitting multi-wavelength lasers according to the embodiment of the present disclosure.

FIG. 1 is a configuration diagram of the apparatus for emitting multi-wavelength lasers according to the embodiment of the present disclosure; FIG. 2 is a configuration diagram of a temperature control part in the apparatus for emitting multi-wavelength lasers according to the embodiment of the present disclosure; and FIG. 3 is a configuration diagram of a cooling part in the apparatus for emitting multi-wavelength lasers according to the embodiment of the present disclosure.

Figure 3:
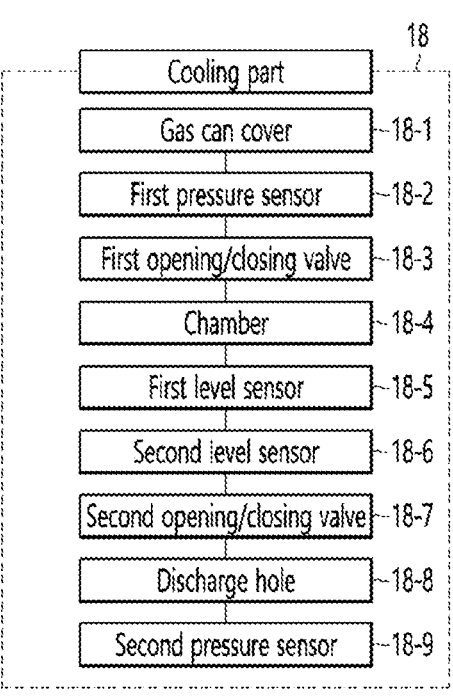
FIG. 3 is a configuration diagram of a cooling part in the apparatus for emitting multi-wavelength lasers according to the embodiment of the present disclosure.

Referring to FIGS. 1 to 3, the apparatus for emitting multi-wavelength lasers includes a main body 10 configured to perform overall control and operation, a handpiece 20 operated by the control of the main body 10 and connected to the main body 10 by wire, and a tip 30 capable of being coupled to one side of the handpiece 20.

The main body 10 includes: a first power supply part 11 configured to enable overall operation; a display part 12 that operates by receiving power from the first power supply part 11 and provides a detailed procedure screen and a detailed procedure setting control screen to a patient and an operator; a control part 13 that operates by receiving power from the first power supply part 11 and controls the overall operation according to a detailed procedure setting value of the display part 12; a laser generation part 14 that receives power from the first power supply part 11, operates according to the control of the control part 13, and generates a laser; the temperature control part 15 that operates by receiving power from the first power supply part 11 and maintains an appropriate temperature to increase laser output efficiency when generating a laser in the laser generation part 14; and the cooling part 18 that operates by receiving power from the first power supply part 11 and outputs cooling gas to a patient's skin.

The main body 10 and the handpiece 20 are wired to each other, and in the present disclosure, it is preferable to transfer a laser generated by the laser generation part 14 of the main body 10 to the handpiece 20 through an optical fiber.

The display part 12 provides a patient with a UI for a detailed setting, and the patient may adjust a detailed laser output setting in the display part 12. In addition, the display part 12 controls the output of a laser and the stop of the laser output and displays errors occurring in the operation of the apparatus to an operator and a patient.

The control part 13 controls the overall operation of the main body and the handpiece when the display part 12 detects a laser output, stopping of the laser output, and a detailed laser setting.

The laser generation part 14 consists of a first laser generator 14-1 and a second laser generator 14-2 that output lasers of different wavelengths. In the embodiment of the present disclosure, it is preferable that the first laser generator 14-1 outputs a laser of a 755 nm wavelength and the second laser generator 14-2 outputs a laser of 1064 nm wavelength, but this is not limiting.

Each of the first laser generator 14-1 and the second laser generator 14-2 includes multiple lamps; a gain medium configured to absorb light generated from the lamps; and a reflection part having one pair of mirrors facing each other at horizontally opposite ends of the gain medium to resonate light on the gain medium. In this case, the gain medium of the first laser generator is Nd: YAG, and the gain medium of the second laser generator is alexandrite.

Each of the reflection parts has a different reflectance, with one mirror of the first laser generator having a reflectance of at least 97% and the other mirror thereof having a reflectance of 78% to 83%. One mirror of the second laser generator has a reflectance of at least 97%, and the other mirror thereof has a reflectance of 38% to 43%.

In this case, instead of the reflection part, the opposite ends of the gain medium may be used by being coated by applying the same reflectances as described above.

The temperature control part 15 includes a first temperature control part 16 for controlling the temperature of the first laser generator, and a second temperature control part 17 for controlling the temperature of the second laser generator.

The first temperature control part 16 includes: a first cooling water chamber 16-1 which provides or accommodates cooling water circulating through a pipe inside the first laser generator in order to maintain the temperatures of the lamps of the first laser generator and the gain medium at appropriate temperatures; a first heating part 16-2 which increases the temperature of the first cooling water chamber 16-1; and a first cooling fan 16-3 which decreases the temperature of the first cooling water chamber 16-1. The second temperature control part 17 includes: a second cooling water chamber 17-1 which provides or accommodates cooling water circulating through a pipe inside the second laser generator in order to maintain the temperatures of the lamps of the second laser generator and the gain medium at appropriate temperatures; a second heating part 17-2 which increases the temperature of the second cooling water chamber 17-1; and a second cooling fan 17-3 which decreases the temperature of the second cooling water chamber 17-1.

The cooling part 18 includes: a gas can cover 18-1 which is attached inside the main body and into which a gas can is inserted; a first hose (not shown) coupled to the lower end of the gas can cover 18-1 and used as a flow path through which gas of the gas can flows; a first pressure sensor 18-2 which is coupled to the lower part of the gas can cover 18-1, operates with power from the first power supply part 11, and checks whether the gas can is inserted into the gas can cover 18-1; the chamber 18-4 which is coupled to one side of the first hose and stores cooling gas; a first opening/closing valve 18-3 which controls gas output in the center portion of the first hose except for the opposite ends of the first hose located between the gas can cover 18-1 and the chamber 18-4 and operates with the power of the first power supply part 11 and control of the control part 13; a first level sensor 18-5 which is coupled to one side of the upper end of the chamber 18-4, detects whether there is gas therein, and operates with the power of the first power supply part 11 and the control of the control part 13; a second level sensor 18-6 which is coupled to one side of the lower end of the chamber 18-4, detects whether there is gas therein, and operates with the power of the first power supply part 11 and the control of the control part 13; a discharge hole 18-8 which is coupled to one side surface of the chamber 18-4 and is configured to discharge gas in the chamber 18-4 to the outside; a second opening/closing valve 18-7 which opens the discharge hole 18-8 to discharge gas in the chamber 18-4 to the outside and operates with the power of the first power supply part 11 and the control of the control part 13; a second pressure sensor 18-9 which is coupled to a lower end of the inner center of the chamber 18-4 and checks whether there is gas in the chamber 18-4; and a second hose (not shown) which connects the chamber 18-4 with the handpiece 20 and is used as a flow path of cooling gas.

When outputting cooling gas through the cooling part 18, first, the gas can is coupled to the inside of the gas can cover 18-1, and when the first pressure sensor 18-2 checks that the gas can is coupled, the control part 13 controls gas of the gas can to be output by opening the first opening/closing valve 18-3.

When gas is output from the gas can, the gas is filled in the chamber 18-4 through the first hose, and when sensing values of both the second level sensor 18-6 and the first level sensor 18-5 of the chamber are detected, the first opening/closing valve 18-3 is closed and the gas output of the gas can is stopped. In this case, it is determined that gas is filled up to the first level sensor 18-5.

When a laser is emitted and a cooling gas is output, the gas filled in the chamber 18-4 is output to a nozzle 24 of the handpiece 20 through the second hose, and when this process is repeated, the sensing value of the first level sensor 18-5 of the chamber 18-4 is not detected first, but the first opening/closing valve 18-3 is closed until the sensing value of the second level sensor 18-6 is not detected.

When the sensing value of the second level sensor 18-6 is not detected, it is determined that there is no gas in the chamber 18-4, and the first opening/closing valve 18-3 is opened to allow the chamber 18-4 to be refilled with the cooling gas of the gas can until the sensing value of the first level sensor 18-5 is detected.

In this case, when there is no change in the sensing value of the first pressure sensor 18-2 and the sensing value of the second pressure sensor 18-9, it is determined that gas inside the gas can is exhausted, and a gas can replacement notification is output through the display part 12. The first pressure sensor 18-2 detects the weight of the gas can and the weight of gas inside the gas can, and when there is no change in the sensing value thereof, it is determined that the cooling gas inside the gas can is exhausted. However, when there is a change in the sensing value of the second pressure sensor 18-9 even if it is determined that there is no change in the sensing value of the first pressure sensor 18-2, there is residual gas in the chamber 18-4 the chamber 18-4. Accordingly, when gas can replacement notification is output to the display part 12 only because there is no change in the sensing value of the first pressure sensor 18-2, a procedure is required to be stopped even though there is residual gas. Accordingly, when it is determined that there is no change in the sensing values of both the first pressure sensor 18-2 and the second pressure sensor 18-9, the gas can replacement notification is output through the display part 12.

When it is detected that there is no change in the sensing values of both the first pressure sensor 18-2 and the second pressure sensor 18-9, gas can replacement notification is output to the display part 12. Since the pressure of the cooling part 18 rises due to internal heat generated by the operation of the structures of the main body 10, the second opening/closing valve 18-7 is opened to release pressure in the chamber 18-4 through the discharge hole 18-8 to the outside. The pressure of the cooling part 18 is reduced by discharging the pressure in the chamber 18-4 through the discharge hole 18-8. After that, a new gas can is coupled to the gas can cover 18-1 and the chamber is filled with gas until a sensing value of the first level sensor 18-5 is detected.

In addition, the control part 13 of the main body 10 controls a third opening/closing valve 23 of the handpiece 20 according to a preset output amount of cooling gas to output the cooling gas through the nozzle 24.

The handpiece 20 includes a housing 21 for protecting internal components from external impact; a second power supply part 22 which is provided in the housing 21 and receives power by being wired to the first power supply part 11 of the main body 10; the third opening/closing valve 23 which operates by receiving power from the second power supply part 22 and is opened by control of the control part 13 to output cooling gas output from the cooling part 18 of the main body 10; the nozzle 24 through which cooling gas is ejected depending on whether the third opening/closing valve 23 is opened or closed; a controller 25 which is located on one surface of the housing 21 of the handpiece 20 and is capable of controlling detailed procedure set values and overall operation; and a corrective lens 26 which is provided on one end of the handpiece 20 and corrects a dispersed laser beam output through optical fiber to be parallel.

The controller 25 is configured in any one of a touch method and a button method.

The tip 30 includes: a housing 31 for protecting internal components from external impact; a detachable member 32 provided on one side of the housing 31 and detachable from the handpiece 20; a lens part 33 provided inside the housing 31 and outputting a laser generated in the main body 10, with the laser having a preset laser output spot size; and a support part 34 that is coupled to one side of the housing 31 and keeps an operator's skin and laser irradiation length constant.

The lens part 33 of the tip 30 includes one or more and less than five lenses therein, wherein the lens may be formed to be concave on one surface thereof and convex on a remaining surface thereof, to be concave on the opposite surfaces thereof, or to be convex on the opposite surfaces, and the lenses may be combined according to the size of a laser irradiation beam.

In one embodiment, when outputting a beam of size of 20 mm size, a dispersed laser beam is collimated by the corrective lens 26 of the handpiece 20, and the size of the beam is adjusted by the combination of the lenses of the lens part 33 of the tip 30. In this case, the two lenses are combined, wherein one lens is formed to be convex on one surface thereof and concave on the other surface thereof, and the other lens is formed to be concave on opposite surfaces thereof.

Next, the method for emitting multi-wavelength lasers according to the embodiment of the present disclosure will be described in detail with reference to the accompanying drawings.

Figure 5:
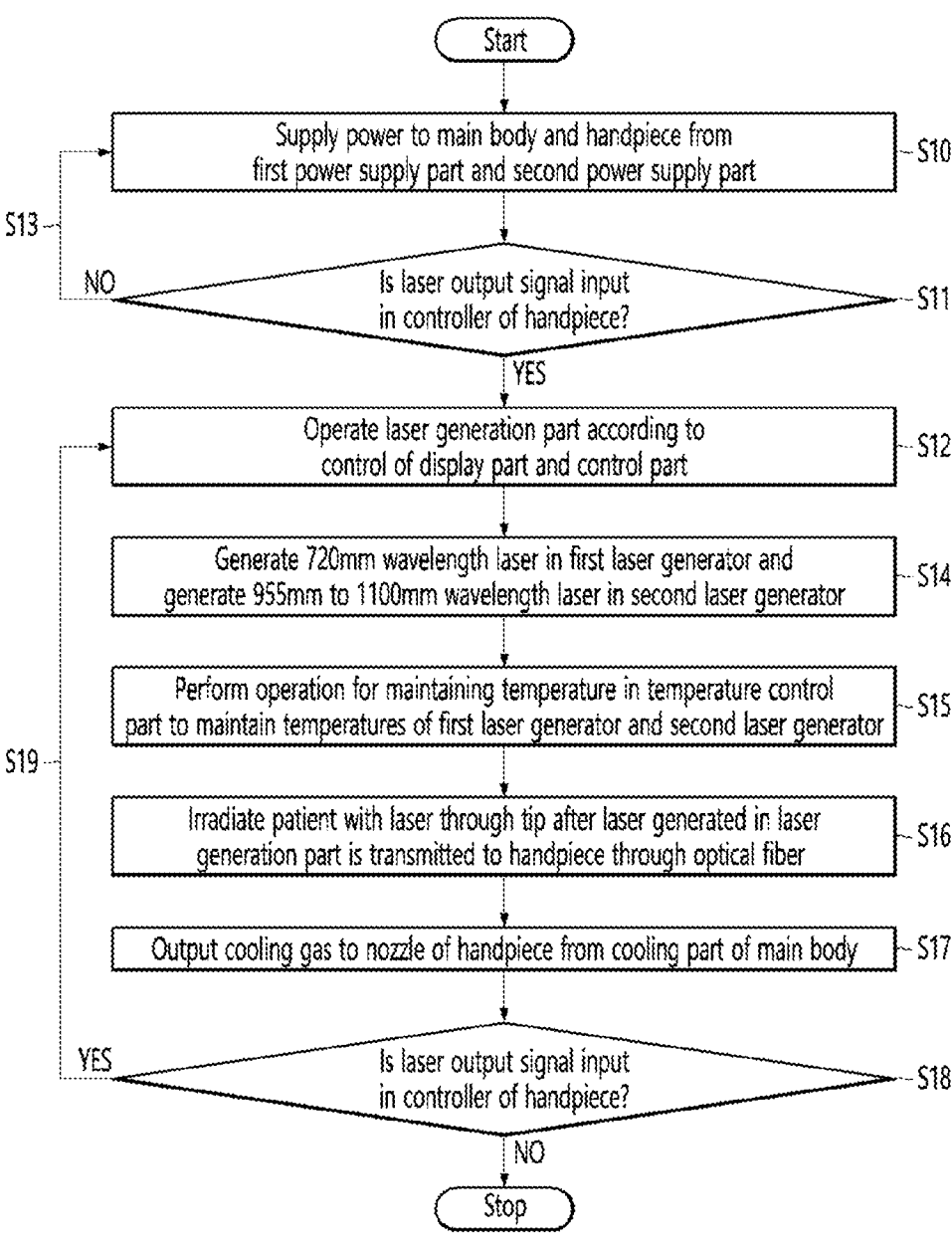
FIG. 5 is a flowchart of a method for emitting multi-wavelength lasers according to the embodiment of the present disclosure.
Figure 6:
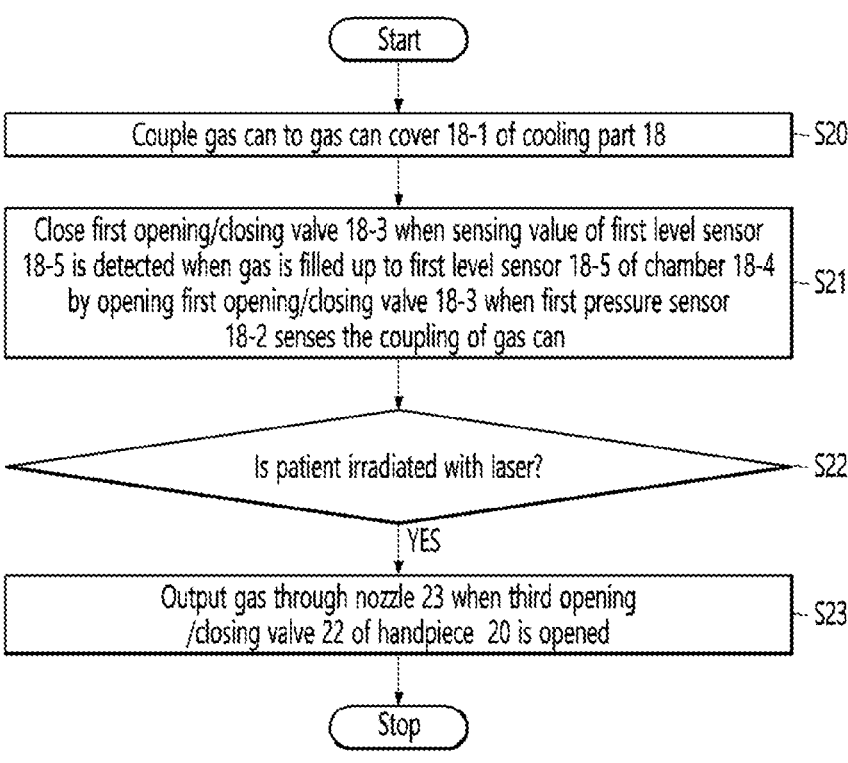
FIG. 6 is a flowchart of a method for outputting cooling gas in the method for emitting multi-wavelength lasers according to the embodiment of the present disclosure.

FIG. 5 is a flowchart of the method for emitting multi-wavelength lasers according to the embodiment of the present disclosure; FIG. 6 is a flowchart of a method for outputting cooling gas in the method for emitting multi-wavelength lasers according to the embodiment of the present disclosure; and FIG. 7 is a flowchart of a method for controlling pressure in a main body in the method for emitting multi-wavelength lasers according to the embodiment of the present disclosure.

Referring to FIGS. 5 to 7, first, the first power supply part 11 of the main body 10 is turned on, and transmits power to the second power supply part 22 of the handpiece 20 at S10.

The controller 25 of the handpiece 20 determines whether a laser output signal is input at S11. In this case, a footswitch or the display part 12 as well as the controller 25 of the handpiece 20 may perform output control.

In the determining of whether a laser output signal is input in the controller 25 of the handpiece 20 at S11, when it is determined that the laser output signal is input, the laser generation part 14 operates according to controls of the display part 12 and the control part 13 and generates a laser at S12.

In the determining of whether a laser output signal is input in the controller 25 of the handpiece 20 at S11, when a laser output signal is not input, the first power supply part 11 of the main body 10 is turned on, and in the transmitting of power to the second power supply part 22 of the handpiece 20 at S10, waiting is performed at S13.

The laser generation part 14 operates according to the control of the display part 12 and the control part 13. The first laser generator 14-1 generates a laser with a wavelength of 720 nm to 780 nm, and the second laser generator 14-2 generates a laser with wavelengths from 955 nm to 1100 nm at S14. In this case, in the present disclosure, it is preferable that a laser generated by the first laser generator 14-1 is a laser of a 755 nm wavelength and a laser generated by the second laser generator 14-2 is a laser of a 1064 nm wavelength, but this is not limiting.

When the first laser generator 14-1 and the second laser generator 14-2 generate lasers, the temperature control part 15 performs an operation for maintaining a temperature to maintain the appropriate temperatures of the laser generators at S15. In this case, the temperature control part 15 includes the first temperature control part 16 which controls the temperature of the first laser generator 14-1, and the second temperature control part 17 which controls the temperature of the second laser generator 14-2.

The first temperature control part 16 maintains the temperature of the first laser generator 14-1 at 50° C. to 65° C., and the second temperature control part 17 maintains a temperature of the second laser generator 14-2 at 20° C. to 35° C. In the embodiment of the present disclosure, the first laser generator 14-1 preferably has a temperature of 50° C. and the second laser generator 14-2 preferably has a temperature of 29° C., but this is not limiting.

When lasers are generated in the first laser generator 14-1 and the second laser generator 14-2. heat is generated therein. The first laser generator 14-1 and the second laser generator 14-2 include temperature sensors (not shown), respectively, to detect the heat. The first laser generator 14-1 and the second laser generator 14-2 are cooled and heated by cooling water flowing inside each of the laser generators. For this reason, the first temperature control part 16 increases the temperature of the cooling water by heating the first cooling water chamber 16-1 with the first heating part 16-2 in order to maintain the temperature of the first laser generator 14-1 at an appropriate temperature 50° C. When the temperature of the first laser generator 14-1 exceeds 50° C. when detected by the temperature sensor, the first cooling water chamber 16-1 is cooled by using the first cooling fan 16-3 to decrease the temperature of the cooling water.

The second temperature control part 17 decreases the temperature of cooling water by cooling the second cooling water chamber 17-1 by using the second cooling fan 17-3 in order to maintain the temperature of the second laser generator 14-2 at an appropriate temperature 19° C. When the temperature of the second laser generator 14-2 is below 29° C. when detected by the temperature sensor, the second cooling water chamber 17-1 is heated by the second heating part 17-2 to increase the temperature of cooling water.

When the first laser generator 14-1 and the second laser generator 14-2 generate lasers, the temperature control part 15 performs an operation for maintaining a temperature to maintain appropriate temperatures of the laser generators at S15, and then a laser generated in the laser generation part 14 is transmitted to the handpiece 20 through an optical fiber, and a patient is irradiated with the transmitted laser through the tip 30 at S16.

In this case, as the lasers with which a patient is irradiated, a laser with a wavelength of 720 nm to 780 nm generated by the first laser generator 14-1 and a laser with a wavelength of 955 nm to 1100 nm generated by the second laser generator 14-2 are simultaneously emitted. In the present disclosure, it is preferable that the laser generated by the first laser generator 14-1 is a 755 nm wavelength laser and the laser generated by the second laser generator 14-2 is a 1064 nm wavelength laser, but this is not limiting.

As the lasers with which the patient is irradiated, the laser with a wavelength of 720 nm to 780 nm generated by the first laser generator 14-1 and the laser with a wavelength of 955 nm to 1100 nm generated by the second laser generator 14-2 the first laser generator 14-1 may be emitted simultaneously or with a time difference of 200 ms therebetween, but this is not limiting.

In this case, the handpiece 20 collimates a diverted laser beam with the corrective lens 26 before transmitting the laser beam to the tip 30.

After irradiating a patient with a laser through the tip 30 at S16, the cooling part 18 of the main body 10 outputs cooling gas to the nozzle 24 of the handpiece 20 at S17.

After the outputting of cooling gas to the nozzle 24 of the handpiece 20 at S17, the controller 25 of the handpiece 20 determines whether a laser output signal is input at S18.

In the determining of whether a laser output signal is input in the controller 25 of the handpiece 20 at S18, when it is determined that a laser output signal is input, the laser generation part 14 is operated according to the controls of the display part 12 and the control part 13 in order to return to the generating S12 of a laser at S19.

In the determining of whether a laser output signal is input in the controller 25 of the handpiece 20 at S18, when a laser output signal is not input, laser output is stopped. In this case, power of the apparatus is not completely turned off, but the first power supply part 11 of the main body 10 is turned on, and in the transmitting of power to the second power supply part 22 of the handpiece 20 at S10, waiting is performed.

In the outputting of cooling gas to the nozzle 24 of the handpiece 20 from the cooling part 18 of the main body 10 at S17, first, a gas can is coupled to the gas can cover 18-1 of the cooling part 18 of the main body 10 at S20.

When the gas can is coupled to the gas can cover at S20 and the coupling of the gas can is sensed by the first pressure sensor 18-2, the first opening/closing valve 18-3 is opened, gas is filled up to the first level sensor 18-5 of the chamber 18-4, and when a sensing value of the first level sensor 18-5 is detected, the first opening/closing valve 18-3 is closed S21. In this case, gas is filled from the second hose connected to the third opening/closing valve 23 of the handpiece 20 to the first level sensor 18-5.

Next, in the control part 13 of the main body 10, it is determined whether laser emission is performed on a patient at S22.

In the determining of whether laser emission is performed on the patient at S22, when it is determined that a laser is emitted, the third opening/closing valve 23 of the handpiece 20 is opened and gas is output to the patient through the nozzle 24 at S23.

Because of this, heat generated when laser emission is performed on a patient's skin can be cooled by a cooling gas to prevent burns and to relieve pain.

After the third opening/closing valve 23 of the handpiece 20 is opened and gas is output to a patient through the nozzle 24 at S23, it is determined whether there is the amount of change in the values of the first pressure sensor 18-2 and the second pressure sensor 18-9 at S30.

In the determining of whether there is the amount of change in the values of the first pressure sensor 18-2 and the second pressure sensor 18-9 at S30, when it is determined that there is no amount of change, it is determined that gas inside a gas can is exhausted at S31. In this case, the second opening/closing valve 18-7 of the chamber 18-4 is opened, and the discharge hole 18-8 is opened so as to match atmospheric pressure in the chamber with external atmospheric pressure at S32.

After the third opening/closing valve 23 of the handpiece 20 is opened and gas is output to a patient through the nozzle 24 at S23, it is determined whether the value of the first pressure sensor 18-2 decreases at S40.

In the determining of whether the value of the first pressure sensor 18-2 decreases at S40, when it is determined that the value of the first pressure sensor 18-2 decreases, the heating wire of the gas can cover 18-1 is turned on to increase pressure inside the gas can at S41.

After the third opening/closing valve 23 of the handpiece 20 is opened and gas is output to a patient through the nozzle 24 at S23, it is determined whether there is a sensing value of the second level sensor 18-6 at S50.

In the determining of whether there is a sensing value of the second level sensor 18-6 at S50, when it is determined that there is the sensing value of the second level sensor 18-6, the first opening/closing valve 18-3 is opened and gas is filled until a sensing value of the first level sensor 18-5 is detected at S51.

The determining of whether there is the amount of change in the values of the first pressure sensor 18-2 and the second pressure sensor 18-9 at S30, the determining of whether the value of the first pressure sensor 18-2 decreases at S40, and the determining of whether there is the sensing value of the second level sensor 18-6 at S50 are continuously performed after the first power supply part 11 of the main body 10 is turned on and power is transmitted to the second power supply part 22 of the handpiece 20 at S10.

Because of this, pressure inside the main body 10 is prevented from being higher than external pressure, thereby preventing an explosion of the gas can or an error in gas injection. In addition, the inside of the cooling part is continuously filled with cooling gas, thereby preventing the inconvenience of stopping a procedure.

Although the embodiment of the present disclosure have been described in detail above, the scope of the present disclosure is not limited thereto, and various modifications and improvements by those skilled in the art by using the basic concept of the present disclosure defined in the following claims also fall within the scope of the present disclosure.

What is claimed is:

1. An apparatus for emitting multi-wavelength laser beams, the apparatus comprising:
   a main body configured to perform overall control and operation;
   a handpiece which is operated by the control of the main body and is connected to the main body by wire; and
   a tip capable of being coupled to one side of the handpiece,
   wherein the main body comprises:
   a first power supply part configured to enable the overall operation;
   a display part which operates by receiving power from the first power supply part and provides a procedure screen and a procedure setting control screen to a patient and an operator;
   a control part which operates by receiving power from the first power supply part and controls the overall operation according to a procedure setting value of the display part;
   a laser beam generation part, which receives power from the first power supply part, operates according to the control of the control part, and generates a laser beam;
   a temperature control part which operates by receiving power from the first power supply part and maintains an appropriate temperature to increase laser beam output efficiency when generating the laser beam in the laser beam generation part; and
   a cooling part which operates by receiving power from the first power supply part and outputs cooling gas to a patient's skin,
   wherein the laser beam generation part comprises a first laser beam generator and a second laser beam generator which output laser beams of different wavelengths, respectively, and the temperature control part comprises a first temperature control part which controls a temperature of the first laser beam generator to be within a first predetermined temperature range using a first cooling/heating water which flows inside the first laser beam generator, and a second temperature control part which controls a temperature of the second laser beam generator to be within a second predetermined temperature range using a second cooling/heating water which flows inside the second laser beam generator,
   wherein the first temperature control part is configured to,
   in response to detecting that the temperature of the first laser beam generator is higher than the first predetermined temperature range, cool the first cooling/heating water, and
   in response to detecting that the temperature of the first laser beam generator is lower than the first predetermined temperature range, heat the first cooling/heating water,
   wherein the second temperature control part is configured to,
   in response to detecting that the temperature of the second laser beam generator is higher than the second predetermined temperature range, cool the second cooling/heating water, and
   in response to detecting that the temperature of the second laser beam generator is lower than the second predetermined temperature range, heat the second cooling/heating water,
   wherein the cooling part comprises:
   a gas can cover which is attached inside the main body and into which a gas can is inserted;
   a first hose which is coupled to a lower end of the gas can cover and is used as a flow path through which gas of the gas can flows;
   a first pressure sensor which is coupled to a lower part of the gas can cover, operates with power from the first power supply part, and checks whether the gas can is inserted into the gas can cover;
   a cooling gas chamber which is coupled to one side of the first hose and stores cooling gas;
   a first opening/closing valve which controls gas output in a center portion of the first hose except for opposite ends of the first hose located between the gas can cover and the cooling gas chamber and operates with the power of the first power supply part and the control of the control part;
   a first level sensor which is coupled to one side of an upper end of the cooling gas chamber, detects whether there is gas therein, and operates with the power of the first power supply part and the control of the control part;
   a second level sensor which is coupled to one side of a lower end of the cooling gas chamber, detects whether there is gas therein, and operates with the power of the first power supply part and the control of the control part;
   a discharge hole which is coupled to one side surface of the cooling gas chamber and is configured to discharge gas in the cooling gas chamber to the outside;
   a second opening/closing valve which opens the discharge hole to discharge gas in the cooling gas chamber to the outside and operates with the power of the first power supply part and the control of the control part;

a second pressure sensor which is coupled to a lower end of an inner center of the cooling gas chamber and checks whether there is gas in the cooling gas chamber; and a second hose which connects the cooling gas chamber with the handpiece and is used as a flow path of cooling gas.

2. The apparatus of claim 1, wherein the first laser beam generator generates a laser beam with a wavelength of 720 nm to 780 nm, and the second laser beam generator generates a laser beam with a wavelength of 955 nm to 1100 nm.

3. The apparatus of claim 1, wherein each of the first laser beam generator and the second laser beam generator comprises:

multiple lamps;

a gain medium configured to absorb light generated from the lamps; and a reflection part having one pair of mirrors facing each other at horizontally opposite ends of the gain medium to resonate light on the gain medium.

4. The apparatus of claim 3, wherein one mirror of the first laser beam generator has a reflectance of at least 97%, and one remaining mirror thereof has a reflectance of 78% to 83%.

5. The apparatus of claim 3, wherein one mirror of the second laser beam generator has a reflectance of at least 97%, and one remaining mirror thereof has a reflectance of 38% to 43%.

6. The apparatus of claim 1, wherein each of the first laser beam generator and the second laser beam generator comprises:

multiple lamps; and a gain medium configured to absorb light generated from the lamps, wherein horizontal opposite ends of the gain medium are configured to face each other and coated by applying reflectances to resonate light on the gain medium.

7. The apparatus of claim 1, wherein the first temperature control part comprises:

a first cooling/heating water chamber which provides or accommodates the first cooling/heating water circulating through a pipe inside the first laser beam generator to increase and decrease temperatures of a lamp and a gain medium of the first laser beam generator;

a first heating part which increases a temperature of the first cooling/heating water chamber; and a first cooling fan which decreases the temperature of the first cooling/heating water chamber, and the second temperature control part comprises:

a second cooling/heating water chamber which provides or accommodates the second cooling/heating water circulating through a pipe inside the second laser beam generator to increase and decrease temperatures of a lamp and a gain medium of the second laser beam generator;

a second heating part which increases a temperature of the second cooling/heating water chamber; and a second cooling fan which decreases the temperature of the second cooling/heating water chamber.

8. The apparatus of claim 1, wherein the handpiece comprises a corrective lens which is provided on one end of the handpiece and corrects a dispersed laser beam to be parallel.

9. The apparatus of claim 1, wherein the tip comprises a lens part for outputting a laser beam generated in the main body, with the laser beam having a preset laser beam output spot size.

10. The apparatus of claim 9, wherein the lens part of the tip comprises one or more and less than five lenses therein, wherein each of the lenses is formed to be concave on one surface thereof and convex on a remaining surface thereof, to be concave on the opposite surfaces thereof, or to be convex on the opposite surfaces, and the lenses are combined according to a size of a laser beam irradiation beam.

11. A method for emitting multi-wavelength laser beams, the method comprising:

transmitting power to a second power supply part of a handpiece after a first power supply part of a main body is turned on;

determining whether a laser beam output signal is input in a controller of the handpiece;

generating a laser beam by operating a laser beam generation part according to controls of a display part and a control part when it is determined that a laser beam output signal is input in the controller of the handpiece;

generating a laser beam with a wavelength of 720 nm to 780 nm in a first laser beam generator and generating a laser beam with a wavelength of 955 nm to 1100 nm in a second laser beam generator, with the laser beam generation part operating according to the controls of the display part and the control part;

performing an operation for maintaining a temperature in a temperature control part to maintain appropriate temperatures of the first and second laser beam generators when the first laser beam generator and the second laser beam generator generate the laser beams;

irradiating a patient with a laser beam generated in the laser beam generation part through a tip after the laser beam is transmitted through an optical fiber to the handpiece;

outputting cooling gas to a nozzle of the handpiece from a cooling part of the main body;

determining whether a laser beam output signal is input in the controller of the handpiece; and returning to the generating of a laser beam by operating the laser beam generation part according to the controls of the display part and the control part when it is determined that a laser beam output signal is input in the controller of the handpiece, wherein the outputting of cooling gas to the nozzle of the handpiece from the cooling part of the main body comprises:

coupling a gas can to a gas can cover of the cooling part of the main body;

closing a first opening/closing valve when a sensing value of a first level sensor is detected after the first opening/closing valve is opened and gas is filled up to the first level sensor of a chamber when the gas can is coupled to the gas can cover and the coupling of the gas can is sensed by a first pressure sensor;

determining whether a patient is irradiated with a laser beam in the control part of the main body; and outputting gas to a patient through the nozzle by opening a third opening/closing valve of the handpiece when it is determined that the patient is irradiated with the laser beam.

12. The method of claim 11, wherein in the performing of the operation for maintaining a temperature in the temperature control part to maintain the appropriate temperatures of the laser beam generators, the temperature control part comprises a first temperature control part which controls the temperature of the first laser beam generator, and a second temperature control part which controls the temperature of the second laser beam generator.

13. The method of claim 12, wherein the first temperature control part maintains the temperature of the first laser beam generator at 50° C. to 65° C., and the second temperature control part maintains the temperature of the second laser beam generator at 20° C. to 35° C.

14. The method of claim 11, further comprising:

collimating a dispersed laser beam by using a corrective lens before the handpiece transmits a laser beam to the tip in the irradiating of a patient with a laser beam generated in the laser beam generation part through the tip after the laser beam is transmitted through the optical fiber to the handpiece.

15. The method of claim 11, wherein the outputting of gas to a patient through the nozzle by opening the third opening/closing valve of the handpiece comprises:

determining whether there is an amount of change in values of the first pressure sensor and a second pressure sensor;

determining that gas inside the gas can is exhausted when it is determined that there is no amount of change in the values of the first pressure sensor and the second pressure sensor in the determining of whether there is the amount of change in the values of the first pressure sensor and the second pressure sensor; and matching atmospheric pressure inside the chamber with external atmospheric pressure by opening a second opening/closing valve of the chamber and a discharge hole.

16. The method of claim 11, wherein in the irradiating a patient with a laser beam generated in the laser beam generation part through the tip after the laser beam is transmitted through the optical fiber to the handpiece, the laser beam with a wavelength of 720 nm to 780 nm generated in the first laser beam generator and the laser beam with a wavelength of 955 nm to 1100 nm generated in the second laser beam generator are emitted simultaneously.

17. The method of claim 11, wherein in the irradiating a patient with a laser beam generated in the laser beam generation part through the tip after the laser beam is transmitted through the optical fiber to the handpiece, the laser beam with a wavelength of 720 nm to 780 nm generated in the first laser beam generator and the laser beam with a wavelength of 955 nm to 1100 nm generated in the second laser beam generator are emitted simultaneously or with a time difference of 200 ms therebetween.

* * * * *